(12) United States Patent
King et al.

(10) Patent No.: US 12,256,740 B2
(45) Date of Patent: *Mar. 25, 2025

(54) MICROORGANISMS FOR PLANT PATHOGEN INHIBITION

(71) Applicant: MICROBIAL DISCOVERY GROUP, LLC, Franklin, WI (US)

(72) Inventors: Michael R. King, Oak Creek, WI (US); Sona Son, Cudahy, WI (US); Amy Lange, Greendale, WI (US); Megan Duersteler, Franklin, WI (US); Elizabeth Galbraith, Franklin, WI (US)

(73) Assignee: MICROBIAL DISCOVERY GROUP, LLC, Franklin, WI (US)

( * ) Notice: Subject to any disclaimer, the term of this patent is extended or adjusted under 35 U.S.C. 154(b) by 42 days.

This patent is subject to a terminal disclaimer.

(21) Appl. No.: 18/300,126

(22) Filed: Apr. 13, 2023

(65) Prior Publication Data

US 2023/0284631 A1 Sep. 14, 2023

Related U.S. Application Data

(63) Continuation of application No. 16/585,023, filed on Sep. 27, 2019, now Pat. No. 11,627,741.

(60) Provisional application No. 62/738,208, filed on Sep. 28, 2018.

(51) Int. Cl.
| | |
|---|---|
| *A01N 63/22* | (2020.01) |
| *A01N 25/12* | (2006.01) |
| *C12N 1/20* | (2006.01) |
| *C12R 1/07* | (2006.01) |

(52) U.S. Cl.
CPC ............. *A01N 63/22* (2020.01); *A01N 25/12* (2013.01); *C12N 1/20* (2013.01); *C12N 1/205* (2021.05); *C12R 2001/07* (2021.05)

(58) Field of Classification Search
CPC ........ A01N 63/22; A01N 25/12; C12N 1/205; C12R 2001/07
See application file for complete search history.

(56) References Cited

U.S. PATENT DOCUMENTS

| | | | |
|---|---|---|---|
| 4,673,638 A | 6/1987 | Grosch et al. | |
| 5,587,475 A | 12/1996 | Helquist et al. | |
| 5,665,354 A | 9/1997 | Neyra | |
| 8,025,874 B2 | 9/2011 | Bellot et al. | |
| 8,540,981 B1 | 9/2013 | Wehnes et al. | |
| 11,627,741 B2 * | 4/2023 | King ...................... | C12N 1/205 424/93.46 |
| 2005/0255092 A1 | 11/2005 | Rehberger et al. | |
| 2006/0188978 A1 | 8/2006 | Grant | |
| 2009/0280090 A1 | 11/2009 | Rehberger et al. | |
| 2010/0010080 A1 | 1/2010 | Mockett et al. | |
| 2010/0062021 A1 | 3/2010 | Winkelman | |
| 2010/0092428 A1 | 4/2010 | Schmidt et al. | |
| 2012/0100118 A1 | 4/2012 | Rehberger et al. | |
| 2012/0315258 A1 | 12/2012 | Rehberger et al. | |
| 2013/0064927 A1 | 3/2013 | Davis et al. | |
| 2013/0100118 A1 | 4/2013 | Mlyniec et al. | |
| 2013/0136695 A1 | 5/2013 | Hargis et al. | |
| 2013/0295067 A1 | 11/2013 | Baltzley et al. | |
| 2015/0079058 A1 | 3/2015 | Nielsen et al. | |
| 2015/0111214 A1 | 4/2015 | Liu | |
| 2015/0147303 A1 | 5/2015 | Hsieh | |
| 2015/0216203 A1 | 8/2015 | Isaksen et al. | |
| 2015/0216916 A1 | 8/2015 | Galbraith et al. | |
| 2017/0079308 A1 | 3/2017 | King et al. | |
| 2017/0246224 A1 * | 8/2017 | King ...................... | A23K 20/10 |
| 2017/0327840 A1 | 11/2017 | Bayer | |
| 2019/0021341 A1 | 1/2019 | Davis et al. | |

FOREIGN PATENT DOCUMENTS

| | | |
|---|---|---|
| CA | 2948832 A1 | 11/2015 |
| CN | 101159102 A | 4/2008 |
| CN | 102223809 A | 10/2011 |
| CN | 103980535 B | 12/2017 |
| GB | 1434582 A | 5/1976 |
| WO | 2012/009712 A2 | 1/2012 |
| WO | 2014/020141 A1 | 2/2014 |
| WO | 2014/067081 A1 | 5/2014 |
| WO | 2015/160960 A1 | 10/2015 |
| WO | 2015/175667 A1 | 11/2015 |
| WO | 2017/081105 A1 | 5/2017 |
| WO | 2017/151608 A1 | 9/2017 |
| WO | 2018/148847 A1 | 8/2018 |

OTHER PUBLICATIONS

Choudhary et al. 2009 (Interactions of *Bacillus* spp. and plants—with special reference to induced systemic resistance (ISR); Microbiological Research 164: 493-513) (Year: 2009).*
Karigar et al., "Role of Microbial Enzymes in the Bioremediation of Pollutants: A Review," Enzyme Research, vol. 2011, Article ID 805187, 11 pages.
Schmidt et al., "New Concepts of microbial treatment processes for the nitrogen removal in wastewater," 2003.
Ramachandran et al., "A Broad-Spectrum Antimicrobial Activity of Bacillus subtilis RLID 12.1," 2014.
International search report and written opinion for PCT/US2017/019941, dated May 26, 2017.
Kiarie et al. "The Role of Added Feed Enzymes in Promoting Gut Health in Swine and Poultry," Nutrition Research Reviews, Jun. 1, 2013 (Jun. 1, 2013), vol. 26, pp. 71-88.

(Continued)

*Primary Examiner* — Mary Maille Lyons
(74) *Attorney, Agent, or Firm* — Barnes & Thornburg LLP (57) ABSTRACT

The invention relates to treatment of a plant with one or more microorganisms for inhibiting a plant pathogen. More particularly, the invention relates to isolated *Bacillus* strains, and strains having all of the identifying characteristics of these strains, and combinations thereof, for a use comprising the above-mentioned use.

17 Claims, 2 Drawing Sheets
Specification includes a Sequence Listing.

(56) References Cited

OTHER PUBLICATIONS

La Ragione et al. "Bacillus subtilis Spores Competitively Exclude *Escherichia coli* 078: K80 in Poultry," Veterinary Microbiology, Mar. 20, 2001 (Mar. 20, 2001) vol. 79, pp. 133-142.
Harnentis et al. "Isolation, Characterization and Production of Mannanase from Thermophilic Bacteria to Increase the Feed Quality," Pakistan Journal of Nutrition 12 (4): 360-364, 2013.
PCT Search Report and Written Opinion for PCT/US2015/030578, completed Jul. 9, 2015.
Extended European Search Report, U.S. Appl. No. 15/792,802. 9-1358 dated Nov. 8, 2017, 8 pages.
Souza et al. J. Anim. Sci. vol. 90, Suppl. 3/J. Dairy Sci. vol. 95, suppl. 2 T281.
Credille et al. (2014). Prevalence of bacteremia in dairy cattle with acute puerperal metritis. J Vet Intern Med, 28:1606-1612.
Sheldon et al. (2009). Defining postpartum uterine disease and the mechanisms of infection and immunity in the female reproductive tract in cattle. Biol Re rod 81:1025-1032.
Abutarbush et al. (2005). Jejunal hemorrhage syndrome in dairy and beef cattle: 11 cases (2001 to 2003). Can. Vet. J. Rev. Vét. Can. 46, 711-715.
Abutarbush et al. (2004). Jejunal hemorrhage syndrome in 2 Canadian beef cows. Can. Vet. J. 45, 48-50.
Adaska et al. (2014). Jejunal hematoma in cattle: a retrospective case analysis. J. Vet. Diagn. Investig. Off. Publ. Am. Assoc. Vet Lab Diagn. Inc 26, 96-103.
Baines et al. (2011). Mouldy feed, mycotoxins and Shiga toxin-producing *Escherichia coli* colonization associated with Jejunal Hemorrhage Syndrome in beef cattle. BMC Vet. Res. 7, 24.
Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of Clostridium perfringens Type A in the Disease Complex. J. Vet. Med. Ser. A 53, 518-523.
Dennison et al. (2002). Hemorrhagic bowel syndrome in dairy cattle: 22 cases (1997-2000). J. Am. Vet. Med. Assoc. 221, 686-689.
Dennison et al. (2005). Comparison of the odds of isolation, genotypes, and in vivo production of major toxins by Clostridium perfringens obtained from the gastrointestinal tract of dairy cows with hemorrhagic bowel syndrome or left-displaced abomasum. J. Am. Vet. Med. Assoc. 227, 132-138.
Malinen et al. (2003). Comparison of real-time PCR with SYBR Green I or 5'-nuclease assays and dot-blot hybridization with rDNA-targeted oligonucleotide probes in quantification of selected faecal bacteria. Microbiology. 149: 269-277.
West et al. (2007) Rapid Detection of *Escherichia coli* Virulence Factor Genes using Multiplex Real-Time TaqMan@ PCR Assays. Veterinary Microbiology 122(3-4): 323-331.
Frydendahl et al. (2001). Automated 5' nuclease assay for detection of virulence factors in porcine *Escherichia coli*. Molec.Cell. Probes. 15: 151-160.
Nielsen et al. (2003). Detection and characterization of verocytotoxin-producing *Escherichia coli* by automated 5 nuclease PCR assay, Journal of ClinicalMicrobiology, vol. 41, No. 7, pp. 2884 2893.
Jinneman et al. (2003). Multiplex Real-Time PCR Method to Identify Shiga Toxin Genes stx1 and stx2 and *Escherichia coli* 0157:H7/H--Serotype. Appl. Environ. Microbiol. Oct. 2003 vol. 69 No. 10 6327-6333.
Yatsuyanagi et al. (2002). Characterization of enteropathogenic and enteroaggregative *Escherichia coli* isolated from diarrheal outbreaks, Journal of Clinical Microbiology, vol. 40, No. 1, pp. 294-297.
Albini et al. (2010). Real-time multiplex PCR assays for reliable detection of Clostridium perfringens toxin genes in animal isolates, Veterinary Microbiology, 127 (1-2): 179-185.
Johnson et al. (2012). A MIQE-Compliant Real-Time PCR Assay for Aspergillus Detection., PLOSone., 7(7): 1-8.
International search report and written opinion for PCT/US2018/058948, dated Jan. 18, 2019.
Miller et al., "Sanitary Landfill Simulation: Test Parameters and a Simulator Conceptual Design," Naval Facilities Engineering Command: Civil Engineering Laboratory, Oct. 20, 1976 (Oct. 20, 1976), pp. 1-47. Retrieved from the Internet: <https://apps.dtic.mil/dtic/tr/fulltext/u2/a030998.pdf>.
Fei et al., "A laboratory landfill simulator for physical, geotechnical, chemical and microbial characterization of solid waste biodegradation processes," Couples Phenomena in Environmental Geotechnics, May 20, 2013 (May 20, 2013), Taylor & Francis Group, London, pp. 321-327.
Mahar et al., "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.

* cited by examiner

SEQUENCE LISTING

```
Sequence total quantity: 2
SEQ ID NO: 1            moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 1
tccgtaggtg aacctgcgg                                                              19

SEQ ID NO: 2            moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 2
tcctccgctt attgatatgc                                                             20
```

MICROORGANISMS FOR PLANT PATHOGEN INHIBITION

CROSS-REFERENCE TO RELATED APPLICATIONS

This application is a continuation of U.S. application Ser. No. 16/585,023, filed on Sep. 27, 2019, which claims priority under 35 U.S.C. § 119(e) to U.S. Provisional Application Ser. No. 62/738,208 filed on Sep. 28, 2018, the entire disclosure of which is incorporated herein by reference.

SEQUENCE LISTING

Incorporated by reference in its entirety is a computer-readable nucleotide/amino acid Sequence Listing which has been submitted electronically herewith and identified as follows: as a 4 kilobytes xml file named "299804.xml", created on Apr. 4, 2023.

FIELD OF THE DISCLOSURE

The invention relates to treatment of a plant with one or more microorganisms for inhibiting a plant pathogen. More particularly, the invention relates to isolated *Bacillus* strains, and strains having all of the identifying characteristics of these strains, and combinations thereof, for a use comprising the above-mentioned use.

BACKGROUND AND SUMMARY OF THE INVENTION

The present invention relates to microorganisms, such as isolated *Bacillus* strains for use in inhibiting plant pathogens. Fungal pathogens cause a variety of diseases in plants, including, but not limited to, basal stem rot disease caused by *Ganoderma boninense*, bud rot caused by *Phytophthora palmivora*, and wilt caused by *Fusarium oxysporum*. These diseases detrimentally affect palm plants on oil palm plantations, and cause significant economic losses in the palm oil industry. An additional fungal species, *Cladosporium cladosporioides* causes *Cladosporium* rot in the leaves and fruit of many plants, most notably red wine grapevines. *C. cladosporioides* affects up to 50% of grape clusters at harvest, greatly reducing yield and detrimentally impacting wine quality. Yeasts such as *Pichia manshurica*, which grow on the fruit surface can contribute to off-odors and wine spoilage also resulting in loss of wine quality and financial loss. *Aspergillus fumigatus* is a ubiquitous mold that is commonly found on decaying vegetation and is not only a problem as an agent of soft rot, but has also been established as the global leading cause of aspergillosis in humans and causes one of the highest numbers of deaths among patients with fungal infections. Many other fungal diseases have detrimental effects on plants and cause significant economic losses in the horticulture, agricultural, and forestry industries in general, for example. *Ralstonia solanacearum* is a soil-borne bacterial strain that causes bacterial wilt in a wide range of host plants.

Applicants have developed *Bacillus* strains, and combinations thereof, that are useful for inhibiting plant pathogens. These strains comprise *Bacillus* strains selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

In one embodiment, a method of treating a plant to inhibit a fungal or a bacterial disease is provided. The method comprises contacting the plant with a composition comprising an effective amount of an isolated *Bacillus* strain selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof, and inhibiting the fungal disease or the bacterial disease.

In another embodiment, a commercial package is provided. The commercial package comprises an isolated *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18

(NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

In yet another embodiment, a composition is provided comprising an isolated *Bacillus* strain selected from the group consisting of *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of treating a plant to inhibit a fungal disease or a bacterial disease, the method comprising contacting the plant with a composition comprising an effective amount of an isolated *Bacillus* strain selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof, and inhibiting the fungal disease or the bacterial disease.

2. The method of clause 1 wherein the *Bacillus* strain is selected from the group consisting of *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain A12 (NRRL No. B-67516), a strain having all of the identifying characteristics of *Bacillus* strain A12 (NRRL No. B-67516), *Bacillus* strain 1607 (NRRL No. B-67666), a strain having all of the identifying characteristics of *Bacillus* strain 1607 (NRRL No. B-67666), and combinations thereof.

3. The method of clause 1 or 2 wherein the *Bacillus* strain is selected from the group consisting of *Bacillus* strain 300 (NRRL No. B-50943), a strain having all of the identifying characteristics of *Bacillus* strain 300 (NRRL No. B-50943), *Bacillus* strain 235 (NRRL No. B-67219), a strain having all of the identifying characteristics of *Bacillus* strain 235 (NRRL No. B-67219), *Bacillus* strain 1607 (NRRL No. B-67666), a strain having all of the identifying characteristics of *Bacillus* strain 1607 (NRRL No. B-67666), and combinations thereof.

4. The method of clause 2 wherein the *Bacillus* strain is *Bacillus* strain 300 (NRRL No. B-50943).

5. The method of clause 2 where the *Bacillus* strain is *Bacillus* strain 235 (NRRL No. B-67219).

6. The method of clause 2 wherein the *Bacillus* strain is *Bacillus* strain 1607 (NRRL No. B-67666).

7. The method of clause 2 wherein the *Bacillus* strain is *Bacillus* strain 101 (NRRL No. B-67218).

8. The method of clause 2 wherein the *Bacillus* strain is *Bacillus* strain 77 (NRRL No. B-67274).

9. The method of any one of clauses 1 to 8 wherein the *Bacillus* strain has antifungal activity.

10. The method of any one of clauses 1 to 9 wherein the fungal disease is caused by a fungus of a genus selected from the group consisting of *Ganoderma*, *Phytophthora*, *Fusarium*, and combinations thereof.

11. The method of clause 10 wherein the fungal disease is caused by a fungus selected from the group consisting of *Ganoderma boninense*, *Ganoderma mirabile*, *Ganoderma weberianum*, *Phytophthora palmivora*, *Fusarium kyushuense*, *Fusarium oxysporum*, *Fusarium nelsonii*, *Cladosporium cladosporioides*, *Pichia manshurica*, *Pichia kudriavzevii*, *Aspergillus fumigatus*, and combinations thereof.

12. The method of clause 11 wherein the fungus is *Ganoderma boninense*.

13. The method of clause 11 wherein the fungus is *Ganoderma mirabile*.

14. The method of clause 11 wherein the fungus is *Ganoderma weberianum*.

15. The method of clause 11 wherein the fungus is *Phytophthora palmivora*.

16. The method of clause 11 wherein the fungus is *Fusarium kyushuense*.

17. The method of clause 11 wherein the fungus is *Fusarium oxysporum*.

18. The method of clause 11 wherein the fungus is *Fusarium nelsonii*.

19. The method of any one of clauses 1 to 18 further comprising treating the plant with a different *Bacillus* strain, a lactic acid bacterial strain, and combinations thereof.

20. The method of any one of clauses 1 to 19 wherein the effective amount of the *Bacillus* strain is about $1.0 \times 10^2$ CFU/ml or gram of the composition used to contact the plant to about $1.0 \times 10^8$ CFU/ml or gram of the composition used to contact the plant.

21. The method of any one of clauses 1 to 19 wherein the effective amount of the *Bacillus* strain is about $1.0 \times 10^2$ CFU/ml or gram of the composition used to contact the plant to about 1.0×10⁴ CFU/ml or gram of the composition used to contact the plant.

22. The method of any one of clauses 1 to 19 wherein the effective amount is an amount greater than about $1.0 \times 10^2$ CFU/ml or gram of the composition used to contact the plant to about $1.0 \times 10^3$ CFU/ml or gram of the composition used to contact the plant.

23. The method of any one of clauses 1 to 22 wherein the Bacillus strain comprises live Bacillus cells or spores.

24. The method of clause 23 wherein the Bacillus strain comprises live Bacillus cells.

25. The method of clause 23 wherein the Bacillus strain comprises spores.

26. The method of any one of clauses 1 to 25 wherein the composition is a liquid.

27. The method of any one of clauses 1 to 25 wherein the composition is dry.

28. The method of clause 27 wherein the composition is lyophilized.

29. The method of any one of clauses 1 to 28 wherein the contacting is by spraying the composition onto the plant.

30. The method of any one of clauses 1 to 28 wherein the contacting is by manually applying the composition onto the plant.

31. The method of any one of clauses 1 to 30 wherein the plant is contacted by contacting the composition with a part of the plant selected from the group consisting of a leaf, a seed, a root, a flower, a shoot, a bud, and combinations thereof.

32. The method of any one of clauses 1 to 30 wherein the plant is contacted by applying the composition to the soil from which the plant obtains nutrients.

33. The method of any one of clauses 1 to 32 wherein the plant is a palm plant.

34. A commercial package or a composition comprising an isolated Bacillus strain selected from the group consisting of Bacillus strain A12 (NRRL No. B-67516), a strain having all of the identifying characteristics of Bacillus strain A12 (NRRL No. B-67516), Bacillus strain V17 (NRRL No. B-67664), a strain having all of the identifying characteristics of Bacillus strain V17 (NRRL No. B-67664), Bacillus strain V18 (NRRL No. B-67665), a strain having all of the identifying characteristics of Bacillus strain V18 (NRRL No. B-67665), Bacillus strain 1607 (NRRL No. B-67666), a strain having all of the identifying characteristics of Bacillus strain 1607 (NRRL No. B-67666), and combinations thereof.

35. A commercial package or a composition comprising an isolated Bacillus strain used to inhibit a fungal disease or a bacterial disease in a plant wherein the isolated Bacillus strain is selected from the group consisting of Bacillus strain 86 (NRRL No. B-50944), a strain having all of the identifying characteristics of Bacillus strain 86 (NRRL No. B-50944), Bacillus strain 300 (NRRL No. B-50943), a strain having all of the identifying characteristics of Bacillus strain 300 (NRRL No. B-50943), Bacillus strain 101 (NRRL No. B-67218), a strain having all of the identifying characteristics of Bacillus strain 101 (NRRL No. B-67218), Bacillus strain 235 (NRRL No. B-67219), a strain having all of the identifying characteristics of Bacillus strain 235 (NRRL No. B-67219), Bacillus strain 77 (NRRL No. B-67274), a strain having all of the identifying characteristics of Bacillus strain 77 (NRRL No. B-67274), Bacillus strain 177 (NRRL No. B-67275), a strain having all of the identifying characteristics of Bacillus strain 177 (NRRL No. B-67275), Bacillus strain 102 (NRRL No. B-67276), a strain having all of the identifying characteristics of Bacillus strain 102 (NRRL No. B-67276), Bacillus strain ATC2 (NRRL No. B-67134), a strain having all of the identifying characteristics of Bacillus strain ATC2 (NRRL No. B-67134), Bacillus strain A12 (NRRL No. B-67516), a strain having all of the identifying characteristics of Bacillus strain A12 (NRRL No. B-67516), Bacillus strain V17 (NRRL No. B-67664), a strain having all of the identifying characteristics of Bacillus strain V17 (NRRL No. B-67664), Bacillus strain V18 (NRRL No. B-67665), a strain having all of the identifying characteristics of Bacillus strain V18 (NRRL No. B-67665), Bacillus strain 1607 (NRRL No. B-67666), a strain having all of the identifying characteristics of Bacillus strain 1607 (NRRL No. B-67666), and combinations thereof.

36. The commercial package or composition of any one of clauses 34 to 35 wherein the Bacillus strain is in the form of a concentrate.

37. The commercial package or composition of any one of clauses 34 to 35 wherein the Bacillus strain is in the form of a superconcentrate.

38. The commercial package or composition of any one of clauses 34 to 37 wherein the Bacillus strain is in a dry form.

39. The commercial package or composition of any one of clauses 34 to 37 wherein the Bacillus strain is in a form selected from the group consisting of a powder and a liquid.

40. The commercial package or composition of any one of clauses 34 to 39 further comprising a carrier for the Bacillus strain.

41. The commercial package or composition of clause 40 wherein the carrier is selected from the group consisting of salt, a dextrin, and combinations thereof.

42. The commercial package or composition of any one of clauses 34 to 41 in a bag.

43. The commercial package or composition of clause 42 wherein the bag is a plastic bag.

44. The commercial package or composition of any one of clauses 34 to 43 further comprising instructions for use of one or more of the Bacillus strains.

45. The commercial package or composition of any one of clauses 42 to 43 in a 20-pound bag.

46. The commercial package or composition of any one of clauses 42 to 43 in a 50-pound bag.

47. The commercial package or composition of clause 39 wherein the Bacillus strain is in powder form.

48. The commercial package or composition of clause 39 wherein the Bacillus strain is in liquid form.

49. The commercial package or composition of any one of clauses 34 to 48 wherein the Bacillus strain is in a container for commercial use.

50. The commercial package or composition of clause 49 wherein the container comprises plastic.

51. The commercial package or composition of clause 49 wherein the container comprises paper.

52. The commercial package or composition of any one of clauses 34 to 51 further comprising a binder.

53. The commercial package or composition of clause 52 wherein the binder is selected from the group consisting of clay, yeast cell wall components, aluminum silicate, and glucan, or combinations thereof.

54. The commercial package or composition of any one of clauses 34 or 36 to 53 wherein the Bacillus strain is used to inhibit a fungal disease in a plant.

55. The commercial package or composition of any one of clauses 34 or 36 to 53 wherein the Bacillus strain is used to inhibit a bacterial disease in a plant.

56. The method of clause 11 wherein the fungus is Cladosporium cladosporioides.

57. The method of clause 11 wherein the fungus is *Pichia manshurica*.

58. The method of clause 11 wherein the fungus is *Pichia kudriavzevii*.

59. The method of clause 11 wherein the fungus is *Aspergillus fumigatus*.

60. The method of any one of clauses 1 to 33 wherein the bacterial disease is caused by bacteria of the genus *Ralstonia*.

61. The method of clause 60 wherein the bacteria are *Ralstonia solanacearum*.

DETAILED DESCRIPTION OF ILLUSTRATIVE EMBODIMENTS

Applicants have developed *Bacillus* strains, and combinations thereof, that can be used to treat plants to inhibit a fungal disease or a bacterial disease. More particularly, the invention relates to isolated *Bacillus* strains, and strains having all of the identifying characteristics of these strains, and combinations thereof, for a use comprising the abovementioned use. These fungal and bacterial diseases detrimentally affect plants and cause significant economic losses in the horticulture, agricultural, and forestry industries, for example.

In one embodiment, a method of treating a plant to inhibit a fungal disease or a bacterial disease is provided. The method comprises contacting the plant with a composition comprising an effective amount of an isolated *Bacillus* strain selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof, and inhibiting the fungal disease or the bacterial disease.

In another embodiment, a commercial package is provided. The commercial package comprises an isolated *Bacillus* strain selected from the group consisting of *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

In yet another embodiment, a composition is provided comprising an isolated *Bacillus* strain selected from the group consisting of *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof. In another aspect, this *Bacillus* strain composition can be used to inhibit a fungal disease or a bacterial disease in a plant.

In another embodiment, a commercial package or a composition is provided comprising an isolated *Bacillus* strain used to inhibit a fungal disease or a bacterial disease in a plant wherein the isolated *Bacillus* strain is selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No.

B-67666), a strain having all of the identifying characteristics of *Bacillus* strain 1607 (NRRL No. B-67666), and combinations thereof.

The following clauses, and combinations thereof, provide various additional illustrative aspects of the invention described herein. The various embodiments described in this section titled "DETAILED DESCRIPTION OF ILLUSTRATIVE EMBODIMENTS" are applicable to any of the following embodiments of the invention described in the numbered clauses below.

1. A method of treating a plant to inhibit a fungal disease or a bacterial disease, the method comprising contacting the plant with a composition comprising an effective amount of an isolated *Bacillus* strain selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof, and inhibiting the fungal disease or the bacterial disease.

2. The method of clause 1 wherein the *Bacillus* strain is selected from the group consisting of *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain A12 (NRRL No. B-67516), a strain having all of the identifying characteristics of *Bacillus* strain A12 (NRRL No. B-67516), *Bacillus* strain 1607 (NRRL No. B-67666), a strain having all of the identifying characteristics of *Bacillus* strain 1607 (NRRL No. B-67666), and combinations thereof.

3. The method of clause 1 or 2 wherein the *Bacillus* strain is selected from the group consisting of *Bacillus* strain 300 (NRRL No. B-50943), a strain having all of the identifying characteristics of *Bacillus* strain 300 (NRRL No. B-50943), *Bacillus* strain 235 (NRRL No. B-67219), a strain having all of the identifying characteristics of *Bacillus* strain 235 (NRRL No. B-67219), *Bacillus* strain 1607 (NRRL No. B-67666), a strain having all of the identifying characteristics of *Bacillus* strain 1607 (NRRL No. B-67666), and combinations thereof.

4. The method of clause 2 wherein the *Bacillus* strain is *Bacillus* strain 300 (NRRL No. B-50943).

5. The method of clause 2 where the *Bacillus* strain is *Bacillus* strain 235 (NRRL No. B-67219).

6. The method of clause 2 wherein the *Bacillus* strain is *Bacillus* strain 1607 (NRRL No. B-67666).

7. The method of clause 2 wherein the *Bacillus* strain is *Bacillus* strain 101 (NRRL No. B-67218).

8. The method of clause 2 wherein the *Bacillus* strain is *Bacillus* strain 77 (NRRL No. B-67274).

9. The method of any one of clauses 1 to 8 wherein the *Bacillus* strain has antifungal activity.

10. The method of any one of clauses 1 to 9 wherein the fungal disease is caused by a fungus of a genus selected from the group consisting of *Ganoderma, Phytophthora, Fusarium*, and combinations thereof.

11. The method of clause 10 wherein the fungal disease is caused by a fungus selected from the group consisting of *Ganoderma boninense, Ganoderma mirabile, Ganoderma weberianum, Phytophthora palmivora, Fusarium kyushuense, Fusarium oxysporum, Fusarium nelsonii, Cladosporium cladosporioides, Pichia manshurica, Pichia kudriavzevii, Aspergillus fumigatus*, and combinations thereof.

12. The method of clause 11 wherein the fungus is *Ganoderma boninense*.

13. The method of clause 11 wherein the fungus is *Ganoderma mirabile*.

14. The method of clause 11 wherein the fungus is *Ganoderma weberianum*.

15. The method of clause 11 wherein the fungus is *Phytophthora palmivora*.

16. The method of clause 11 wherein the fungus is *Fusarium kyushuense*.

17. The method of clause 11 wherein the fungus is *Fusarium oxysporum*.

18. The method of clause 11 wherein the fungus is *Fusarium nelsonii*.

19. The method of any one of clauses 1 to 18 further comprising treating the plant with a different *Bacillus* strain, a lactic acid bacterial strain, and combinations thereof.

20. The method of any one of clauses 1 to 19 wherein the effective amount of the *Bacillus* strain is about $1.0 \times 10^2$ CFU/ml or gram of the composition used to contact the plant to about $1.0 \times 10^8$ CFU/ml or gram of the composition used to contact the plant.

21. The method of any one of clauses 1 to 19 wherein the effective amount of the *Bacillus* strain is about $1.0 \times 10^2$ CFU/ml or gram of the composition used to contact the plant to about $1.0 \times 10^4$ CFU/ml or gram of the composition used to contact the plant.

22. The method of any one of clauses 1 to 19 wherein the effective amount is an amount greater than about $1.0 \times 10^2$ CFU/ml or gram of the composition used to contact the plant to about $1.0 \times 10^3$ CFU/ml or gram of the composition used to contact the plant.

23. The method of any one of clauses 1 to 22 wherein the *Bacillus* strain comprises live *Bacillus* cells or spores.

24. The method of clause 23 wherein the *Bacillus* strain comprises live *Bacillus* cells.

25. The method of clause 23 wherein the *Bacillus* strain comprises spores.

26. The method of any one of clauses 1 to 25 wherein the composition is a liquid.

27. The method of any one of clauses 1 to 25 wherein the composition is dry.

28. The method of clause 27 wherein the composition is lyophilized.

29. The method of any one of clauses 1 to 28 wherein the contacting is by spraying the composition onto the plant.

30. The method of any one of clauses 1 to 28 wherein the contacting is by manually applying the composition onto the plant.

31. The method of any one of clauses 1 to 30 wherein the plant is contacted by contacting the composition with a part of the plant selected from the group consisting of a leaf, a seed, a root, a flower, a shoot, a bud, and combinations thereof.

32. The method of any one of clauses 1 to 30 wherein the plant is contacted by applying the composition to the soil from which the plant obtains nutrients.

33. The method of any one of clauses 1 to 32 wherein the plant is a palm plant.

34. A commercial package or a composition comprising an isolated *Bacillus* strain selected from the group consisting of *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

35. A commercial package or a composition comprising an isolated *Bacillus* strain used to inhibit a fungal disease or a bacterial disease in a plant wherein the isolated *Bacillus* strain is selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

36. The commercial package or composition of any one of clauses 34 to 35 wherein the *Bacillus* strain is in the form of a concentrate.

37. The commercial package or composition of any one of clauses 34 to 35 wherein the *Bacillus* strain is in the form of a superconcentrate.

38. The commercial package or composition of any one of clauses 34 to 37 wherein the *Bacillus* strain is in a dry form.

39. The commercial package or composition of any one of clauses 34 to 37 wherein the *Bacillus* strain is in a form selected from the group consisting of a powder and a liquid.

40. The commercial package or composition of any one of clauses 34 to 39 further comprising a carrier for the *Bacillus* strain.

41. The commercial package or composition of clause 40 wherein the carrier is selected from the group consisting of salt, a dextrin, and combinations thereof.

42. The commercial package or composition of any one of clauses 34 to 41 in a bag.

43. The commercial package or composition of clause 42 wherein the bag is a plastic bag.

44. The commercial package or composition of any one of clauses 34 to 43 further comprising instructions for use of one or more of the *Bacillus* strains.

45. The commercial package or composition of any one of clauses 42 to 43 in a 20-pound bag.

46. The commercial package or composition of any one of clauses 42 to 43 in a 50-pound bag.

47. The commercial package or composition of clause 39 wherein the *Bacillus* strain is in powder form.

48. The commercial package or composition of clause 39 wherein the *Bacillus* strain is in liquid form.

49. The commercial package or composition of any one of clauses 34 to 48 wherein the *Bacillus* strain is in a container for commercial use.

50. The commercial package or composition of clause 49 wherein the container comprises plastic.

51. The commercial package or composition of clause 49 wherein the container comprises paper.

52. The commercial package or composition of any one of clauses 34 to 51 further comprising a binder.

53. The commercial package or composition of clause 52 wherein the binder is selected from the group consisting of clay, yeast cell wall components, aluminum silicate, and glucan, or combinations thereof.

54. The commercial package or composition of any one of clauses 34 or 36 to 53 wherein the *Bacillus* strain is used to inhibit a fungal disease in a plant.

55. The commercial package or composition of any one of clauses 34 or 36 to 53 wherein the *Bacillus* strain is used to inhibit a bacterial disease in a plant.

56. The method of clause 11 wherein the fungus is *Cladosporium* cladosporioides.

57. The method of clause 11 wherein the fungus is *Pichia manshurica*.

58. The method of clause 11 wherein the fungus is *Pichia* kudriavzevii.

59. The method of clause 11 wherein the fungus is *Aspergillus fumigatus*.

60. The method of any one of clauses 1 to 33 wherein the bacterial disease is caused by bacteria of the genus *Ralstonia*.

61. The method of clause 60 wherein the bacteria are *Ralstonia solanacearum*.

In various embodiments, the *Bacillus* strain for use in accordance with the methods, commercial packages, and compositions described herein can be selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

*Bacillus* strain MDG 101 and *Bacillus* strain MDG 235 were deposited on Jan. 4, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67218 and B-67219, respectively. *Bacillus* strain MGL77, *Bacillus* strain MGL177, and *Bacillus* strain MGL102 were deposited on Jun. 7, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67274, B-67275, and B-67276, respectively. The deposits were made under the provisions of the Budapest Treaty on the International Recognition of the Deposit of Microorganisms for the Purposes of Patent Procedure. The NRRL strain designations are MDG 101, MDG 235, MGL77, MGL177, and MGL102 which are equivalent to *Bacillus* strain 101, 235, 77, 177, and 102 respectively, as referred to in the application.

*Bacillus* strain MDG86 and *Bacillus* strain MDG300 were deposited on Mar. 14, 2014 at the Agricultural Research Service Culture Collection (NRRL), National Center for Agricultural Utilization Research, Agricultural Research Service, USDA, 1815 North University Street, Peoria, Illinois 61604-3999, and were given accession numbers B-50944 and B-50943, respectively. The deposits were made under the provisions of the Budapest Treaty on the International Recognition of the Deposit of Microorganisms for the Purposes of Patent Procedure. The NRRL strain designations are MDG86 and MDG300, which are equivalent to *Bacillus* strain 86 and 300, respectively, as referred to in the application.

*Bacillus* strain ATC2 was deposited on Sep. 16, 2015 at the Agricultural Research Service Culture Collection (NRRL), National Center for Agricultural Utilization Research, Agricultural Research Service, USDA, 1815 North University Street, Peoria, Illinois 61604-3999, and was given accession number B-67134. The deposit was made under the provisions of the Budapest Treaty on the International Recognition of the Deposit of Microorganisms for the Purposes of Patent Procedure. The NRRL strain designation is ATC2, which is equivalent to *Bacillus* strain ATC2, as referred to in the application.

*Bacillus* strain MDGA12 was deposited on Sep. 14, 2017 at the Agricultural Research Service Culture Collection (NRRL), International Depository Authority, 1815 North University Street, Peoria, Illinois 61604, and was given accession number B-67516. The deposit was made under the provisions of the Budapest Treaty on the International Recognition of the Deposit of Microorganisms for the Purposes of Patent Procedure. The NRRL strain designation is MDGA12, which is equivalent to *Bacillus* strain A12, as referred to in the application.

*Bacillus* strains V17, V18, and 1607 were deposited on Aug. 14, 2018 at the Agricultural Research Service Culture Collection (NRRL), International Depository Authority, 1815 North University Street, Peoria, Illinois 61604, and were given accession numbers B-67664, B-67665, and B-67666, respectively. The deposits were made under the provisions of the Budapest Treaty on the International Recognition of the Deposit of Microorganisms for the Purposes of Patent Procedure. The NRRL strain designations are MDGV17, MDGV18, and MDG1607, which are equivalent to *Bacillus* strain V17, V18, and 1607, respectively, as referred to in the application. *Bacillus* strain V17 is a *Bacillus pumilus* strain and *Bacillus* strain 1607 is a *Bacillus amyloliquefaciens* strain, strains 102 and 177 are *Bacillus pumilus* strains, strain 77 is a *Bacillus licheniformis* strain, and all other strains described in the application are *Bacillus subtilus* strains.

In one illustrative aspect, any of these strains can be used to treat plants to inhibit fungal or bacterial infections or diseases alone or in combination in the form of a liquid or dry spray to be applied to the plant or to the soil from which the plant obtains nutrients, or in the form of a liquid or dry composition for manual application to the plant or to the soil from which the plant obtains nutrients. In one embodiment, multiple strains are used to treat the plants in combination in a single composition. In another embodiment, multiple strains are used to treat the plant in combination in separate compositions.

As used herein "a strain having all of the identifying characteristics of" *Bacillus* strain 86, 300, 101, 235, 77, 177, 102, A12, ATC2, V17, V18, or 1607 can be a mutant strain having all of the identifying characteristics of *Bacillus* strain 86, 300, 101, 235, 77, 177, 102, A12, ATC2, V17, V18, or 1607 (e.g., a DNA fingerprint based on DNA analysis that corresponds to the DNA fingerprint of *Bacillus* strain 86, 300, 101, 235, 77, 177, 102, A12, ATC2, V17, V18, or 1607, enzyme activities that correspond to *Bacillus* strain 86, 300, 101, 235, 77, 177, 102, A12, ATC2, V17, V18, or 1607, antimicrobial activity that corresponds to *Bacillus* strain 86, 300, 101, 235, 77, 177, 102, A12, ATC2, V17, V18, or 1607, antibiotic sensitivity and tolerance profiles that correspond to *Bacillus* strain 86, 300, 101, 235, 77, 177, 102, A12, ATC2, V17, V18, or 1607, or combinations thereof). In alternate embodiments, the mutation can be a natural mutation, or a genetically engineered mutation. In another embodiment, "a strain having all of the identifying characteristics of" *Bacillus* strain 86, 300, 101, 235, 77, 177, 102, A12, ATC2, V17, V18, or 1607 can be a strain, for example, produced by isolating one or more plasmids from *Bacillus* strain 86, 300, 101, 235, 77, 177, 102, A12, ATC2, V17, V18, or 1607 and introducing the one or more plasmids into another bacterium, such as another *Bacillus* strain, as long as the one or more plasmids contain DNA that provides the identifying characteristics of *Bacillus* strain 86, 300, 101, 235, 77, 177, 102, A12, ATC2, V17, V18, or 1607 (e.g., a DNA fingerprint based on DNA analysis that corresponds to the DNA fingerprint of *Bacillus* strain 86, 300, 101, 235, 77, 177, 102, A12, ATC2, V17, V18, or 1607).

In another embodiment, one or more of the *Bacillus* strains described in the preceding paragraphs (e.g., *Bacillus* strain 86, 300, 101, 235, 77, 177, 102, A12, ATC2, V17, V18, or 1607) can be used to treat plants along with another bacterial strain selected from the group consisting of a different *Bacillus* strain, a lactic acid bacterial strain, and combinations thereof. In still another embodiment, the additional *Bacillus* strain can be selected from the group consisting of *Bacillus amyloliquefaciens*, *Bacillus lichenifor-*

*mis*, *Bacillus pumilus*, other *Bacillus* strains, and combinations thereof. In yet another embodiment, one or more of the *Bacillus* strains described in the preceding paragraphs (e.g., *Bacillus* strain 86, 300, 101, 235, 77, 177, 102, A12, ATC2, V17, V18, or 1607) can be used to treat plants along with any other bacterial strain effective to treat plants to inhibit a fungal or bacterial infection or a fungal or bacterial disease.

As used herein the terms "inhibit", "inhibiting", and "inhibited" mean to reduce or eliminate the symptoms of a fungal or bacterial disease or a fungal or bacterial infection for the plant or a human, or to reduce or eliminate the number, or an activity, of a fungus or bacterium of a type that causes a fungal or bacterial disease or a fungal or bacterial infection, and which is found in association with the plant or human. Exemplary fungal diseases that can be inhibited using the methods, commercial packages, and compositions described herein are basal stem rot disease, bud rot, wilt, soft rot, *Cladosporium* rot, and aspergillosis. An exemplary bacterial disease is bacterial wilt caused by *Ralstonia solanacearum*. The *Bacillus* strains described herein can also prevent off-odors on fruit, and wine spoilage resulting in loss of wine quality and financial loss.

The compositions described herein can be used to treat plants for any period of time that is effective to inhibit a fungal or bacterial disease or a fungal or bacterial infection and/or to control the detrimental effects of a fungal or bacterial disease or a fungal or bacterial infection. For example, in one embodiment treatment of the plants can occur daily, bi-weekly, three times a week, four times a week, five times a week, once weekly, monthly, or for any suitable time or using any suitable protocol for inhibiting a fungal or bacterial disease or a fungal or bacterial infection. The time periods for treatment of the plants are non-limiting and it should be appreciated that any time period or treatment schedule determined to be effective to inhibit a fungal or bacterial disease or a fungal or bacterial infection and/or control the detrimental effects of a fungal or bacterial disease or a fungal or bacterial infection may be used.

In various illustrative embodiments, the *Bacillus* strain (e.g., *Bacillus* strain 86, 300, 101, 235, 77, 177, 102, A12, ATC2, V17, V18, or 1607), or any other bacterial strains added in addition to *Bacillus* strain 86, 300, 101, 235, 77, 177, 102, A12, ATC2, V17, V18, or 1607, can be used to treat plants at about $1.0 \times 10^2$ CFU, about $1.0 \times 10^2$ CFU to about $1.0 \times 10^3$ CFU, about $1.0 \times 10^2$ CFU to about $1.0 \times 10^4$ CFU, about $1.0 \times 10^2$ CFU to about $1.0 \times 10^5$ CFU, about $1.0 \times 10^2$ CFU to about $1.0 \times 10^6$ CFU, about $1.0 \times 10^2$ CFU to about $1.0 \times 10^7$ CFU. about $1.0 \times 10^2$ CFU to about $1.0 \times 10^8$ CFU, about $1.0 \times 10^2$ CFU to about $1.0 \times 10^9$ CFU, about $1.0 \times 10^2$ CFU to about $1.0 \times 10^{10}$ CFU, about $1.0 \times 10^3$ CFU to about $5.0 \times 10^{12}$ CFU or at about $1.0 \times 10^3$ CFU to about $1.0 \times 10^{10}$ CFU. In other embodiments, the *Bacillus* strain (e.g., *Bacillus* strain 86, 300, 101, 235, 77, 177, 102, A12, ATC2, V17, V18, or 1607) can be used to treat the plants at an amount greater than or about $1.0 \times 10^2$ CFU, at greater than or about $1.0 \times 10^3$ CFU, at greater than or about $1.1 \times 10^3$ CFU, at greater than or about $1.25 \times 10^3$ CFU, at greater than or about $1.5 \times 10^3$ CFU, at greater than or about $1.75 \times 10^3$ CFU, at greater than or about $1.0 \times 10^4$ CFU, at greater than or about $2.0 \times 10^4$ CFU, at greater than or about $3.0 \times 10^4$ CFU, at greater than or about $4.0 \times 10^4$ CFU, at greater than or about $5.0 \times 10^4$ CFU, at greater than or about $6.0 \times 10^4$ CFU, at greater than or about $7.0 \times 10^4$ CFU, at greater than or about $8.0 \times 10^4$ CFU, at greater than or about $1.0 \times 10^5$ CFU, at greater than or about $1.0 \times 10^6$ CFU, at greater than or about $1.0 \times 10^7$ CFU, at greater than or about $1.0 \times 10^8$ CFU, at greater than or about $1.0 \times 10^9$ CFU, at greater than or about $1.0 \times 10^{10}$ CFU, at greater than or about $1.0 \times 10^{11}$ CFU, or at greater than or about $1.0 \times 10^{12}$ CFU. In all of the embodiments using "CFU", the CFU can be CFU/gram or CFU/ml of the liquid or powdered formulation applied to the plants.

In various illustrative aspects, the fungi that can be inhibited include a fungus of a genus selected from the group consisting of *Ganoderma*, *Phytophthora*, *Fusarium*, *Cladosporium*, *Pichia*, and *Aspergillus*, and combinations thereof, or a fungus selected from the group consisting of *Ganoderma boninense*, *Ganoderma mirabile*, *Ganoderma weberianum*, *Phytophthora palmivora*, *Fusarium kyushuense*, *Fusarium oxysporum*, *Fusarium nelsonii*, *Cladosporium cladosporioides*, *Pichia manshurica*, *Pichia kudriavzevii*, *Aspergillus fumigatus*, and combinations thereof. In some embodiments described herein, the *Bacillus* strains (e.g., *Bacillus* strain 86, 300, 101, 235, 77, 177, 102, A12, ATC2, V17, V18, or 1607) can have antifungal activity. Such antifungal activity can be against, for example, a fungus of a genus selected from the group consisting of *Ganoderma*, *Phytophthora*, *Fusarium*, *Cladosporium*, *Pichia*, and *Aspergillus*, and combinations thereof, or a fungus selected from the group consisting of *Ganoderma boninense*, *Ganoderma mirabile*, *Ganoderma weberianum*, *Phytophthora palmivora*, *Fusarium kyushuense*, *Fusarium oxysporum*, *Fusarium nelsonii*, *Cladosporium cladosporioides*, *Pichia manshurica*, *Pichia kudriavzevii*, *Aspergillus fumigatus*, and combinations thereof. As used herein, *Pichia* are yeast, but can be considered a type of fungus. Other types of yeast (i.e., considered fungi) that may be inhibited by the *Bacillus* species described herein are *Saccharomyces* species, *Kluyveromyces* species, Torulaspora species, *Schizosaccharomyces* species, *Hansenula* species, Torulopsis species, *Candida* species, and *Karwinskia* species. In yet another embodiment, any fungal disease of a plant can be inhibited by the *Bacillus* strains 86, 300, 101, 235, 77, 177, 102, A12, ATC2, V17, V18, or 1607, and a strain having all of the identifying characteristics of the *Bacillus* strains, or combinations thereof, described herein. In still another embodiment, any bacterial disease of a plant can be inhibited by the *Bacillus* strains 86, 300, 101, 235, 77, 177, 102, A12, ATC2, V17, V18, or 1607, and a strain having all of the identifying characteristics of the *Bacillus* strains, or combinations thereof, described herein, such as bacterial wilt caused by *Ralstonia solanacearum*.

In one embodiment, a commercial package is provided comprising an isolated *Bacillus* strain selected from the group consisting of *Bacillus* strain 86, 300, 101, 235, 77, 177, 102, A12, ATC2, V17, V18, or 1607, a strain having all of the identifying characteristics of any of these *Bacillus* strains, and combinations thereof.

In another embodiment, a composition is provided comprising an isolated *Bacillus* strain selected from the group consisting of *Bacillus* strain 86, 300, 101, 235, 77, 177, 102, A12, ATC2, V17, V18, or 1607, a strain having all of the identifying characteristics of any of these *Bacillus* strains, and combinations thereof.

In yet another embodiment, a commercial package or a composition is provided comprising an isolated *Bacillus* strain used to inhibit a fungal or bacterial disease in a plant wherein the isolated *Bacillus* strain is selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No.

B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

In these embodiments the *Bacillus* strain can be in the form of, for example, a liquid or a dry composition, such as a suspension or a lyophilized composition or a powder, a freeze-dried composition, a gel, or a pellet, for example. In one illustrative embodiment, the *Bacillus* strain can be in the form of a powder or a liquid, and can be formulated to be sprayed on or manually applied to the plant or to the soil from which the plant obtains nutrients. In other embodiments, the *Bacillus* strain can be mixed with fertilizer, mixed with soil, or used as a seed coating for contacting the plant or a plant part. Any suitable method known in the art for contacting the plant or the soil with the *Bacillus* strain can be used to achieve any of the effective amounts of *Bacillus* strain 86, 300, 101, 235, 77, 177, 102, A12, ATC2, V17, V18, or 1607, or a strain having all of the identifying characteristics of any of these *Bacillus* strains, or combinations thereof, described herein. In one aspect, the *Bacillus* strain can comprise live *Bacillus* cells or spores. In another illustrative embodiment, the plant can be contacted with the *Bacillus* strain by contacting the *Bacillus* strain with a part of the plant selected from the group consisting of a leaf, a seed, a root, a flower, a shoot, a bud, and combinations thereof.

In illustrative aspects, *Bacillus* strain 86, 300, 101, 235, 77, 177, 102, A12, ATC2, V17, V18, or 1607, or a strain having all of the identifying characteristics of any of these *Bacillus* strains, and combinations thereof, can be in the form of a commercial package, or any other suitable composition. In another illustrative embodiment, the *Bacillus* strain(s) in the commercial package, or other composition can be in the form of a concentrate (e.g., about $1\times10^8$ to about $5\times10^9$ CFU/g) or a superconcentrate (e.g., about $1\times10^{10}$ to about $5\times10^{12}$ CFU/g). In another embodiment, the *Bacillus* strain(s) in the commercial package or other composition can be in a dry form (e.g., a powder), a liquid form, a freeze-dried form, or in the form of a gel, or any other suitable form for application to plants or the soil from which the plant obtains nutrients.

In another illustrative embodiment, the *Bacillus* strain(s) in the commercial package or composition can further comprise a carrier for the *Bacillus* strain(s). In various embodiments, the carrier can be selected from the group consisting of bran, rice hulls, a salt, mineral oil, a dextrin (e.g., maltodextrin), whey, sugar, limestone, dried starch, sodium silico aluminate, vegetable oil, and combinations thereof. In another embodiment, the carrier can be any suitable carrier known in the art for a composition for application to plants to treat plants having a fungal or bacterial disease or infection. In another embodiment, the *Bacillus* strain(s) in the commercial package or composition can further comprise a binder such as clay, yeast cell wall components, aluminum silicate, glucan, or other known binders, and/or micronutrients, including but not limited to, nitrogen and phosphorus. Any of these components can be exogenously added (i.e., not naturally present in combination with the *Bacillus* strains) and any of the compositions described herein can be present in nutrient compositions for plants.

In yet other embodiments, the commercial package or composition comprising an isolated *Bacillus* strain can be for inhibiting a fungal or a bacterial disease, and the *Bacillus* strain can be selected from the group consisting of *Bacillus* strain 86 (NRRL No. B-50944), a strain having all of the identifying characteristics of *Bacillus* strain 86 (NRRL No. B-50944), *Bacillus* strain 300 (NRRL No. B-50943), a strain having all of the identifying characteristics of *Bacillus* strain 300 (NRRL No. B-50943), *Bacillus* strain 101 (NRRL No. B-67218), a strain having all of the identifying characteristics of *Bacillus* strain 101 (NRRL No. B-67218), *Bacillus* strain 235 (NRRL No. B-67219), a strain having all of the identifying characteristics of *Bacillus* strain 235 (NRRL No. B-67219), *Bacillus* strain 77 (NRRL No. B-67274), a strain having all of the identifying characteristics of *Bacillus* strain 77 (NRRL No. B-67274), *Bacillus* strain 177 (NRRL No. B-67275), a strain having all of the identifying characteristics of *Bacillus* strain 177 (NRRL No. B-67275), *Bacillus* strain 102 (NRRL No. B-67276), a strain having all of the identifying characteristics of *Bacillus* strain 102 (NRRL No. B-67276), *Bacillus* strain ATC2 (NRRL No. B-67134), a strain having all of the identifying characteristics of *Bacillus* strain ATC2 (NRRL No. B-67134), *Bacillus* strain A12 (NRRL No. B-67516), a strain having all of the identifying characteristics of *Bacillus* strain A12 (NRRL No. B-67516), *Bacillus* strain V17 (NRRL No. B-67664), a strain having all of the identifying characteristics of *Bacillus* strain V17 (NRRL No. B-67664), *Bacillus* strain V18 (NRRL No. B-67665), a strain having all of the identifying characteristics of *Bacillus* strain V18 (NRRL No. B-67665), *Bacillus* strain 1607 (NRRL No. B-67666), a strain having all of the identifying characteristics of *Bacillus* strain 1607 (NRRL No. B-67666), and combinations thereof.

In another embodiment, the commercial package or composition can be in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container comprising the *Bacillus* strain(s) can comprise plastic, metal, foil, paper, fiber, or cardboard (e.g., a plastic pail, a paper bag, a foil bag, a fiber drum, etc.). The commercial package can further comprise instructions for use of one or more of the *Bacillus* strains.

The following examples are for illustrative purposes only. The examples are non-limiting, and are not intended to limit the invention in any way.

Example 1

Culture Conditions

All fungal cultures were obtained from ATCC and include *Ganoderma boninense* ATCC 204074, *Ganoderma weberianum* ATCC 76753, *Ganoderma mirabile* ATCC 76757, 76537, *Phytophthora palmivora* ATCC 26008, *Phytophthora palmivora* ATCC 52161, *Fusarium oxysporum* ATCC 36870, *Fusarium kyushuense* ATCC 56750, and *Fusarium nelsonii* 201410. *Ganoderma* species were cultured on yeast mold agar, *Phytophthora* species were cultured on tomato juice agar, and *Fusarium* species were cultured on potato dextrose agar. *Bacillus* strains 86, 300, 101, 235, 77, 177, 102, A12, ATC2, V17, V18, or 1607 were cultured on tryptic soy agar.

Example 2

Antifungal Plate Assay

Plates were inoculated with an agar plug of fungal growth placed in the center of the plate. *Bacillus* culture was struck on the plate in two parallel lines on either side of the agar plug at a distance of 3 cm. The plates were incubated at 30° C. until the fungal culture exceeded 6 cm in diameter. Data was recorded at 6 days for all strains except *F. kyushuense*, which was recorded at 12 days. Fungal growth was measured, and inhibition scores were assigned for each *Bacillus* strain. Scores of −, +, ++, or +++ were defined as no inhibition, inhibition of 1 cm fungal growth, inhibition of 2 cm, and inhibition of 3 cm, respectively.

Several *Bacillus* strains had strong antifungal activity against all six fungal strains (see Table 1 below). The top six strains had at least moderate activity against all fungal strains, and were further evaluated for antifungal activity in a broth assay.

TABLE 1

Inhibition of fungal growth by *Bacillus* strains in an antifungal plate assay. Inhibition of more than 3 cm of fungal growth is indicated by "+++", 2 to 3 cm inhibition indicated by "++", 1 to 2 cm inhibition indicated by "+", and no inhibition is indicated by "−."

| | Ganoderma boninense | Ganoderma mirabile | Ganoderma weberianum | Phytophthora palmivora 1 | Phytophthora palmivora 2 | Fusarium kyushuense | Fusarium oxysporum | Fusarium nelsonii |
|---|---|---|---|---|---|---|---|---|
| 77 | +++ | + | +++ | ++ | +++ | ++ | ++ | ++ |
| 1607 | ++ | + | +++ | +++ | +++ | ++ | ++ | ++ |
| ATC2 | +++ | + | +++ | ++ | +++ | ++ | ++ | ++ |
| 300 | +++ | ++ | +++ | ++ | +++ | ++ | ++ | ++ |
| 101 | +++ | + | +++ | ++ | +++ | ++ | ++ | ++ |
| 235 | +++ | ++ | +++ | ++ | +++ | ++ | ++ | + |
| 86 | ++ | + | + | ++ | +++ | + | ++ | + |
| V18 | ++ | + | − | ++ | +++ | + | ++ | + |
| A12 | ++ | + | + | ++ | +++ | + | + | + |
| V17 | ++ | + | ++ | + | +++ | − | + | + |
| 102 | − | + | − | − | +++ | − | − | − |
| 177 | − | + | − | − | ++ | − | − | − |

Example 3

Antifungal Broth Assay

The top performing *Bacillus* strains in the plate assay were evaluated using a broth method. An agar plug of fungal growth was used to inoculate 20 ml of broth media containing 10% cell-free *Bacillus* supernatant. Supernatants were prepared by growing *Bacillus* in tryptic soy broth for 24 hours, centrifuging the culture for 20 minutes at 4000 rpm, and filter-sterilizing the supernatant with a 0.22 μm filter. Fungal cultures were grown at 30° C. for two weeks. Fungal growth was filtered and allowed to dry completely. Total dry fungal weight was recorded, and inhibition was reported as a percentage of the reduction in growth weight compared to controls. *G. mirabile* and *P. palmivora* strains were excluded from the broth assay as they did not grow well in broth media.

Figure 1:
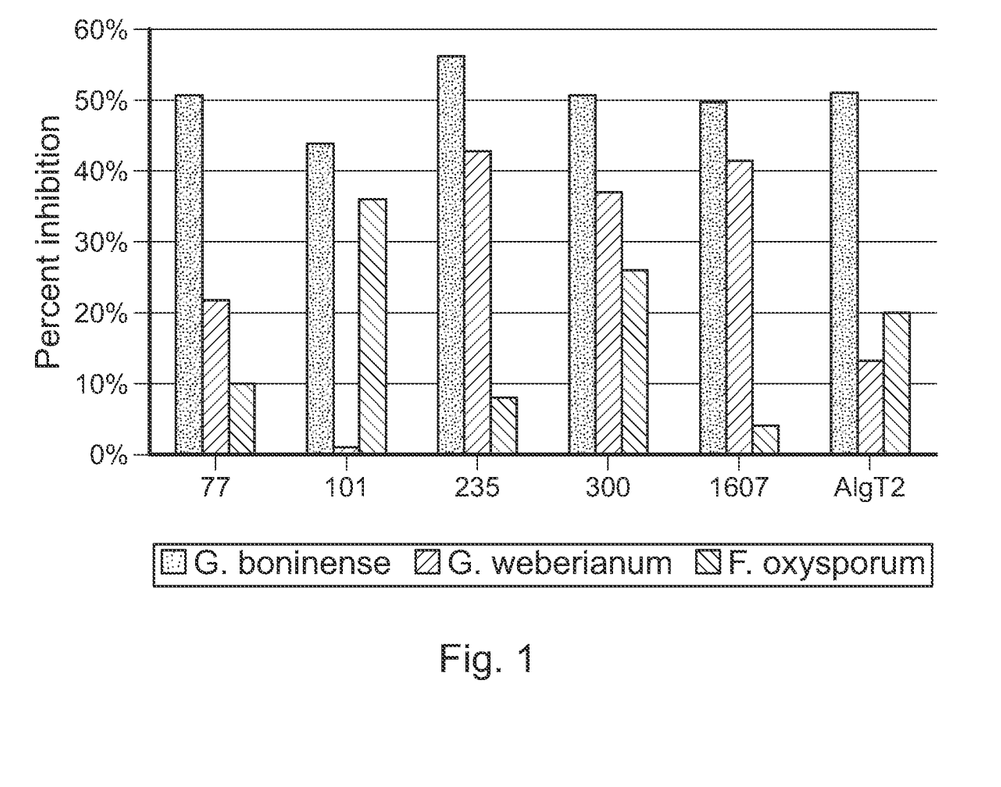
FIG. 1 shows the percent inhibition of growth of *Ganoderma boninense*, *Ganoderma weberianum*, and *Fusarium oxysporum* in broth culture by supernatants from various *Bacillus* strains.

*F. nelsonii* and *F. kyushuense* were not inhibited at all by any *Bacillus* species (data not shown). However, all six *Bacillus* strains inhibited *G. boninense* by over 40%, the pathogen responsible for causing basal stem rot in oil palm plants (see FIG. 1—strain "A1gT2" in FIG. 1 is the same as strain ATC2). *Bacillus* strain 235, 300, and 1607 also had strong activity against *G. weberianum*. *Bacillus* strains 101 and 300 had the best activity against *F. oxysporum*.

Example 4

Isolation and Identification of Additional Pathogenic or Spoilage Fungi

Additional fungal isolates were obtained from molding or rotting vegetation including spoiled corn and hay silage, and were isolated by dilution plating on acidified potato dextrose agar incubated at room temperature (19-21° C.), protected from light, for 2-5 days until distinct isolate growth was observed. DNA was extracted from fungal isolates using the Nucleospin Microbial DNA extraction kit (Machery-Nagel, Duren, Germany), employing a bead-beating step for cell lysis. The fungal ribosomal intergenic spacer (ITS) region was amplified using primers ITS1 (TCCGTAGGT-GAACCTGCGG; SEQ ID NO: 1) and ITS4 (TCCTCCGCTTATTGATATGC; SEQ ID NO: 2) (White, et al., Amplification and direct sequencing of fungal ribosomal RNA genes for phylogenetics, pp. 315-322, In: PCR Protocols: A Guide to Methods and Applications, eds. Innis, et al., Academic Press, Inc., New York (1990), incorporated herein by reference for the amplification method described in this example), following recommended amplification parameters. Product size was determined by gel electrophoresis, the PCR product was cleaned up with the Qiagen MinElute PCR purification kit (Hilden, Germany), and DNA sequencing of each purified PCR product was performed by Eurofins Genomics (Louisville, KY). Sequences were trimmed for quality, in Chromas 2.6 (Technelysium, South Brisbane, Australia) and identified to the closest species match using a nucleotide BLAST search (National Center for Biotechnology Information, Bethesda, Maryland).

Example 5

Antifungal Cross-Streak Assay Using Plant and Spoilage Fungi

Strain-specific antifungal activities of *Bacillus* strains were tested using agar cross-streak antimicrobial susceptibility methods known in the art and described below. Briefly, *Bacillus* strains 77, 86, 300, 101, 235, and V18 were inoculated from frozen glycerol stocks in a single 1 cm wide vertical streak down the center of a non-acidified potato dextrose agar plate. Plates were incubated aerobically for 24 hours at 37° C., or until a confluent streak of *Bacillus* growth was present. Isolates of *Cladosporium, Pichia* and *A. fumigatus* were struck horizontally from the center of the plate, beginning the streak within 1 mm of the *Bacillus* growth and streaking out to the plate perimeter. Plates were incubated at 25° C. under aerobic conditions for 3 days for *Pichia* yeasts and 5 days for the remaining fungal isolates. Zones of inhibition were measured where fungal isolate growth was inhibited by the *Bacillus* strain. Table 2 shows antimicrobial screening utilizing the agar cross streak method against isolates of *Cladosporium cladosporioides*, *Pichia manshurica*, *Pichia kudriavzevii* and *Aspergillus fumigatus*. Scores of –, +, ++, or +++ were defined as no inhibition, inhibition of 2-5 mm fungal growth, inhibition of 5-10 mm, and inhibition of >10 mm, respectively.

Several *Bacillus* strains had broad antifungal activity against all fungal strains tested (see Table 2 below). The top performing *Bacillus* strain was further evaluated for antifungal activity in a broth assay.

Example 7

Inhibition of *Ralstonia Solanacearum* by *Bacillus* Strains

*Ralstonia solanacearum* is a soilborne pathogen that causes bacterial wilt in a variety of crops. Strains of *Ralstonia* were isolated from soil and tested for inhibition of the isolated *Ralstonia* strains by *Bacillus* species. Soil samples were plated for *Ralstonia* species on semi-selective media. Modified SMSA medium contained 1 g/L casein, 10 g/L peptone, 5 ml/L glycerol, and 17 g/L agar at pH 7.0 (Elphinstone et al., 1996). After autoclaving, media was supplemented with 5 mg/L crystal violet, 100 mg/L polymyxin B sulfate, 25 mg/L bacitracin, 5 mg/L chloromycetin,

TABLE 2

Inhibition of fungal growth by *Bacillus* strains in an antifungal cross-streak assay. Inhibition of more than 10 mm of fungal growth is indicated by "+++", 5 to 10 mm inhibition indicated by "++", 2 to 5 mm inhibition indicated by "+", and less than 2 mm inhibition is indicated by "–."

| | | Fungal isolate | | | | | | | |
|---|---|---|---|---|---|---|---|---|---|
| | | *Pichia kudriavzevii* Isolate 1 | *Pichia kudriavzevii* Isolate 2 | *Pichia manschurica* Isolate 1 | *Pichia manschurica* Isolate 2 | *Pichia manschurica* Isolate 3 | *Pichia manschurica* Isolate 4 | *Cladosporium cladosporioides* | *Aspergillus fumigatus* |
| *Bacillus* strain | 77 | ++ | ++ | ++ | ++ | ++ | ++ | +++ | + |
| | 86 | – | – | – | – | – | – | NA | NA |
| | 101 | + | + | + | + | + | ++ | ++ | – |
| | 235 | ++ | ++ | +++ | ++ | ++ | ++ | +++ | + |
| | 300 | ++ | ++ | ++ | ++ | ++ | ++ | +++ | ++ |
| | V18 | – | – | – | – | – | – | +++ | – |

Example 6

*Aspergillus Fumigatus* Antifungal Broth Assay

Figure 2A:
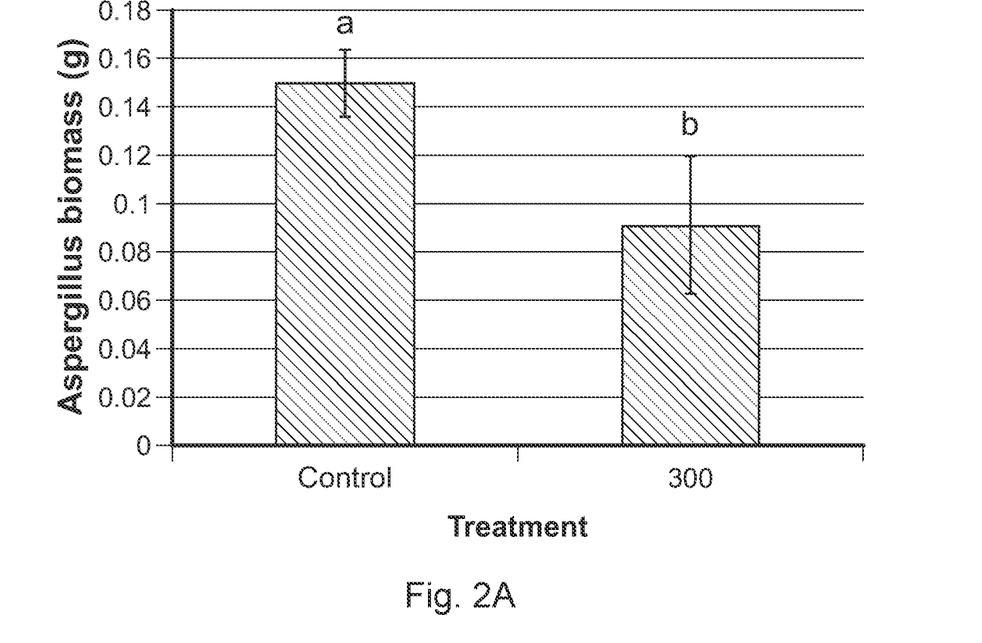
FIG. 2A shows that *Bacillus* strain 300 inhibited *A. fumigatus* biomass accumulation following 24 hours of growth in a liquid broth assay (p=0.02).
Figure 2B:
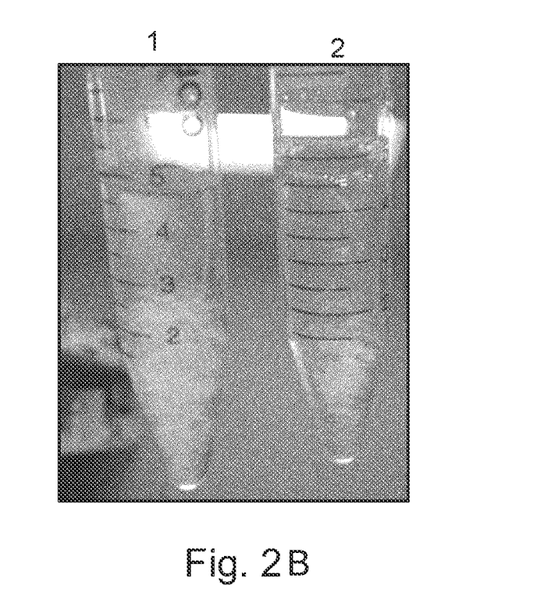
FIG. 2B. is a photograph following 24 hours of *A. fumigatus* growth in liquid broth (tube 1, left) or liquid broth with *Bacillus* strain 300 supernatant (tube 2, right).

The top performing *Bacillus* strain in the plate assay (*Bacillus* strain 300) was evaluated using a broth method to determine efficacy of inhibition of *A. fumigatus* in a liquid matrix. The supernatant was prepared by growing *Bacillus* strain 300 in tryptic soy broth for 24 hours at 32° C., centrifuging the culture for 20 minutes at 4000 rpm, and filter-sterilizing the supernatant with a 0.22 μm filter. *Aspergillus fumigatus* was propagated in potato dextrose broth to produce a suspension of approximately 105 spores/ml. A 0.1 ml amount of this inoculum was used to inoculate 5 ml of potato dextrose broth mixed with 1 ml of sterile-filtered supernatant from *Bacillus* strain 300 or with 1 ml of sterile culture broth (Control). Nine replicates of each treatment were prepared and all replicates were incubated for 24 hr at 37° C. Replicates were pooled into triplicate samples, fungal biomass was sedimented via centrifugation at 4000 rpm for 20 minutes, washed with sterile water to remove media residue, dried on sterile filters and weighed to determine fungal biomass. The photograph shown in FIG. 2B was taken at the end of the 24 hour growth period and the tubes are from left to right, control and *Bacillus* strain 300 treatment. Total dry fungal weight was recorded, and inhibition was reported as a percentage of the reduction in growth weight compared to controls. *Bacillus* strain 300 significantly inhibited *A. fumigatus* biomass (p=0.02), the species associated with acceleration of soft rot in many plant species and which is responsible for opportunistic infections in humans (see FIG. 2A).

0.5 mg/L penicillin, and 100 mg/L cycloheximide. Presumptive *Ralstonia* isolates were identified as *Ralstonia* species by 16S sequencing. *Bacillus* species were tested for antimicrobial activity against the *Ralstonia* species using a cross streak method. The zone of inhibition between the *Bacillus* and *Ralstonia* streak was measured in mm.

As shown in Table 3 below, all *Bacillus* species tested showed some inhibition of all three *Ralstonia* isolates. *Bacillus* species have the potential to be used as biocontrol agents against *Ralstonia* species.

TABLE 3

Inhibition (mm) of *Ralstonia* species by *Bacillus*. The zone of inhibition between the *Bacillus* and *Ralstonia* streak was measured in mm. Inhibition of more than 10 mm growth is indicated by "+++", 6 to 9 mm inhibition is indicated by "++", 1 to 5 mm inhibition is indicated by "+", and no inhibition is indicated by "–".

| *Bacillus* strain | *Ralstonia* species 1 | *Ralstonia* species 2 | *Ralstonia* species 3 |
|---|---|---|---|
| 300 | +++ | +++ | +++ |
| 235 | ++ | +++ | +++ |
| 1607 | ++ | +++ | +++ |
| AlgT2 (equivalent to ATC2) | ++ | +++ | +++ |
| 77 | ++ | ++ | +++ |
| V18 | + | ++ | ++ |
| 101 | ++ | ++ | ++ |
| V17 | ++ | ++ | + |

What is claimed is:

1. A commercial package comprising an isolated *Bacillus* strain selected from the group consisting of *Bacillus* strain MDGV17 (NRRL No. B-67664), *Bacillus* strain MDGV18 (NRRL No. B-67665), *Bacillus* strain MDG1607 (NRRL No. B-67666), and combinations thereof, wherein the *Bacillus* strain is in the form of a powder, a freeze-dried composition, a gel, or a pellet.

2. The commercial package of claim 1 further comprising a carrier for the *Bacillus* strain.

3. The commercial package of claim 2 wherein the carrier is selected from the group consisting of a bran, rice hulls, a salt, mineral oil, a dextrin, whey, sugar, limestone, dried starch, sodium silico aluminate, vegetable oil, and combinations thereof.

4. The commercial package of claim 1 further comprising a binder selected from the group consisting of clay, yeast cell wall components, aluminum silicate, and glucan, or combinations thereof.

5. The commercial package of claim 1 comprising live *Bacillus* strain cells.

6. The commercial package of claim 1 comprising *Bacillus* strain spores.

7. The commercial package of claim 1 wherein said *Bacillus* strain is MDGV17 (NRRL No. B-67664).

8. The commercial package of claim 1 wherein said *Bacillus* strain is MDGV18 (NRRL No. B-67665).

9. The commercial package of claim 1 wherein said *Bacillus* strain is MDG1607 (NRRL No. B-67666).

10. A nutrient composition comprising an isolated *Bacillus* strain selected from the group consisting of *Bacillus* strain MDGV17 (NRRL No. B-67664), *Bacillus* strain MDGV18 (NRRL No. B-67665), *Bacillus* strain MDG1607 (NRRL No. B-67666), and combinations thereof, wherein the *Bacillus* strain is lyophilized.

11. The nutrient composition of claim 10, wherein the lyophilized *Bacillus* strain is in the form of a powder, a freeze-dried composition, a gel, or a pellet.

12. The nutrient composition of claim 11, further comprising an exogenously added micronutrient.

13. The nutrient composition of claim 12, wherein said micronutrient is selected from nitrogen, phosphorus and combinations thereof.

14. The nutrient composition of claim 10, further comprising a binder such as clay, yeast cell wall components, aluminum silicate, glucan, or other known binders.

15. The nutrient composition of claim 14, wherein said *Bacillus* strain is MDGV17 (NRRL No. B-67664), MDGV18 (NRRL No. B-67665), MDG1607 (NRRL No. B-67666) or any combination thereof.

16. A commercial package comprising a bacterial component, wherein said bacterial component comprises
   i) *Bacillus* strain MDG300 (NRRL No. B-50943), and one or more *Bacillus* strains selected from the group consisting of MDGV17 (NRRL No. B-67664), MDGV18 (NRRL No. B-67665), and MDG1607 (NRRL No. B-67666); or
   ii) *Bacillus* strain MDG300 (NRRL No. B-50943), and *Bacillus* strain 1MDG607 (NRRL No. B-67666); or
   iii) *Bacillus* strain MDG235 (NRRL No. B-67219), and one or more *Bacillus* strains selected from the group consisting of MDGV17 (NRRL No. B-67664), MDGV18 (NRRL No. B-67665), and MDG1607 (NRRL No. B-67666); or
   iv) *Bacillus* strain MDG 235 (NRRL No. B-67219), and *Bacillus* strain MDG1607 (NRRL No. B-67666); or
   v) *Bacillus* strain MGL 77 (NRRL No. B-67274), and one or more *Bacillus* strains selected from the group consisting of MDGV17 (NRRL No. B-67664), MDGV18 (NRRL No. B-67665), and MDG1607 (NRRL No. B-67666); or
   vi) *Bacillus* strain MGL 77 (NRRL No. B-67274), and *Bacillus* strain, MDG1607 (NRRL No. B-67666); or
   vii) MDG ATC 2 (NRRL No. B-67134), and one or more *Bacillus* strains selected from the group consisting of MDGV17 (NRRL No. B-67664), MDGV18 (NRRL No. B-67665), and MDG1607 (NRRL No. B-67666); or
   viii) MDG ATC 2 (NRRL No. B-67134), and *Bacillus* strain, MDG1607 (NRRL No. B-67666);
   wherein the bacterial component is in the form of a powder, a freeze-dried composition, a gel, or a pellet.

17. The commercial package of claim 16 further comprising an exogenously added micronutrient.

* * * * *